United States Patent [19]

Franke et al.

[11] Patent Number: 4,612,320
[45] Date of Patent: * Sep. 16, 1986

[54] AMINOPROPANOL DERIVATIVES OF 1-(2-HYDROXYPHENYL)-3-PHENYL-PROPANOLS AND THERAPEUTIC AGENTS CONTAINING THESE COMPOUNDS

[75] Inventors: Albrecht Franke; Josef Gries, both of Wachenheim; Claus D. Müeller, Viernheim; Dieter Lenke, Ludwigshafen, all of Fed. Rep. of Germany

[73] Assignee: BASF Aktiengesellschaft, Fed. Rep. of Germany

[*] Notice: The portion of the term of this patent subsequent to Sep. 10, 2002 has been disclaimed.

[21] Appl. No.: 588,785

[22] Filed: Mar. 12, 1984

[30] Foreign Application Priority Data

Mar. 17, 1983 [DE] Fed. Rep. of Germany ....... 3309595

[51] Int. Cl.$^4$ ................ A61K 31/445; A61K 31/135; C07C 97/10; C07D 295/12; C07D 295/08
[52] U.S. Cl. ..................................... 514/317; 514/327; 514/652; 514/821; 546/217; 546/240; 564/349; 544/401; 544/162; 544/177
[58] Field of Search ................ 424/330, 267; 564/349; 546/240, 217; 514/652, 327, 317, 821

[56] References Cited

U.S. PATENT DOCUMENTS

| | | | |
|---|---|---|---|
| 3,875,149 | 4/1975 | Wooldridge et al. | 260/240 |
| 3,892,799 | 7/1975 | Pinhas | 549/559 |
| 4,263,325 | 4/1981 | Carlsson et al. | 564/349 |
| 4,294,841 | 10/1981 | Champseix et al. | 546/237 |
| 4,460,605 | 7/1984 | Petrik et al. | 564/349 |
| 4,540,697 | 9/1985 | Franke et al. | 514/652 |

FOREIGN PATENT DOCUMENTS

| | | |
|---|---|---|
| 3133814 | 3/1983 | Fed. Rep. of Germany . |
| 3226863 | 4/1983 | Fed. Rep. of Germany . |
| 1307455 | 2/1973 | United Kingdom . |

*Primary Examiner*—Norma S. Milestone
*Attorney, Agent, or Firm*—Keil & Weinkauf

[57] ABSTRACT

Compounds of the general formula

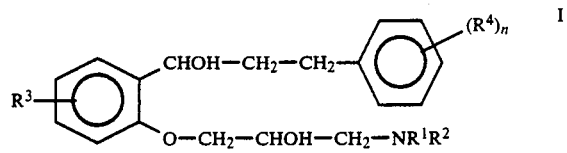

where $R^1$, $R^2$, $R^3$, $R^4$ and n have the meanings given in the description, are useful for treating cardiac disorders.

16 Claims, No Drawings

AMINOPROPANOL DERIVATIVES OF 1-(2-HYDROXYPHENYL)-3-PHENYLPROPANOLS AND THERAPEUTIC AGENTS CONTAINING THESE COMPOUNDS

The present invention relates to novel aminopropanol derivatives of 1-(2-hydroxyphenyl)-3-phenylpropanols and their physiologically tolerated addition compounds with acids, a process for their preparation, and therapeutic agents which contain these compounds and can be used as antiarrhythmics.

German Laid-Open Application DOS No. 2,001,431 discloses that the n-propylamino-, n-butylamino-, sec.-butylamino-and tert.-butylaminopropanol derivatives of 2-hydroxy-$\beta$-phenylpropiophenone possess antiarrhythmic activity. This applies particularly to 2-(2'-hydroxy-3'-n-propylaminopropoxy)-$\beta$-phenylpropiophenone hydrochloride, which is the known antiarrhythmic propafenone. Other compounds structurally similar to propafenone are disclosed in German Laid-Open Applications DOS No. 3,226,863 and DOS No. 3,133,814.

It is an object of the present invention to provide antiarrhythmics which are better than those stated above.

We have found that this object is achieved, and that aminopropanol derivatives of 1-(2-hydroxyphenyl)-3-phenylpropanols of the formula I

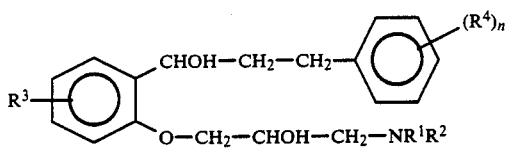

where $R^1$ and $R^2$ are identical or different and are each hydrogen, alkyl, cycloalkyl, alkenyl, alkynyl or hydroxyalkylmethyl, each of not more than 6 carbon atoms, alkoxyalkylmethyl, alkylthioalkylmethyl or dialkylaminoalkylmethyl, each of not more than 9 carbon atoms, or a phenylalkyl or phenoxyalkyl radical where alkyl is of not more than 6 carbon atoms and the phenyl radical is unsubstituted or substituted by alkyl or alkoxy, each of not more than 3 carbon atoms, or $R^1$ and $R^2$, together with the nitrogen atom to which they are bonded, form a 5-membered to 7-membered saturated heterocyclic ring which can be unsubstituted or monosubstituted or disubstituted by phenyl and/or hydroxyl and can contain an oxygen or nitrogen atom as a further hetero atom in the ring, and an additional nitrogen atom may be substituted by alkyl of 1 to 3 carbon atoms or by phenyl, $R^3$ is hydrogen, alkyl of not more than 3 carbon atoms, fluorine, chlorine, bromine, hydroxyl or alkoxy of not more than 6 carbon atoms, $R^4$ is hydrogen, alkyl of not more than 3 carbon atoms, fluorine, chlorine, bromine, hydroxyl, alkoxy of not more than 3 carbon atoms or a radical $NR^5R^6$, where $R^5$ and $R^6$ are identical of different and are each alkyl of not more than 6 carbon atoms or, together with the nitrogen atom to which they are bonded, form a heterocyclic ring, and n is 1 or 2, and their physiologically tolerated addition salts with acids possess useful pharmacological properties.

Among the compounds of the formula I, those in which $R^3$ is hydrogen should be particularly singled out. The group $NR^1R^2$ is preferably a piperidine, piperazine, N-methylpiperazine, morpholine or diisopropylamino radical. Furthermore, $R^1$ and $R^2$ are each, in particular hydrogen or a propyl, butyl, $\beta$-alkoxyalkyl or $\beta$-hydroxyalkyl radical, e.g. n-propyl, isopropyl, n-butyl, isobutyl, tert.-butyl, n-pentyl, sec.-pentyl, isopentyl, neopentyl, $\beta$-methoxyethyl or hydroxyethyl. $R^4$ is preferably hydrogen, hydroxyl, $C_1$–$C_4$-alkoxy, dimethylamino or diethylamino.

Examples of compounds in addition to those stated in the examples are:

1-[2-(2'-Hydroxy-3'-isopropylaminopropoxy)-phenyl]-3-(4'-dimethylaminophenyl)-propanol,
1-[2-(2'-hydroxy-3'-n-butylaminopropoxy)-phenyl]-3-(4'-dimethylaminophenyl)-propanol,
1-[2-(2'-hydroxy-3'-tert.-butylaminopropoxy)-phenyl]-3-(4'-dimethylaminophenyl)-propanol,
1-[2-(2'-hydroxy-3'-(1,1-dimethylpropylamino)-propoxy)phenyl]-3-(4'-dimethylaminophenyl)-propanol,
1-[2-(2'-hydroxy-3'-n-propylaminopropoxy)-phenyl]-3-(3'-dimethylaminophenyl)-propanol,
1-[2-(2'-hydroxy-3'-(1,1-dimethylpropylamino)-propoxy)phenyl]-3-(3'-dimethylaminophenyl)-propanol,
1-[2-(2'-hydroxy-3'-n-propylaminopropoxy)-phenyl]-3-(4'-diethylaminophenyl)-propanol,
1-[2-(2'-hydroxy-3'-piperidinopropoxy)-phenyl]-3-(4'-dimethylaminophenyl)-propanol,
1-[2-(2'-hydroxy-3'-diisopropylaminopropoxy)-phenyl]-3-(4'-dimethylaminophenyl)-propanol,
1-[2-(2'-hydroxy-3'-n-propylaminopropoxy)-5-hydroxyphenyl]-3-phenylpropanol,
1-[2-(2'-hydroxy-3'-n-propylaminopropoxy)-4-hydroxyphenyl]-3-phenylpropanol,
1-[2-(2'-hydroxy-3'-n-propylaminopropoxy)-5-methoxyphenyl]-3-phenylpropanol and
1-[2-(2'-hydroxy-3'-n-propylaminopropoxy)-4-methoxyphenyl]-3-phenylpropanol.

The compounds according to the invention can be prepared by reducing the corresponding aminopropanol derivatives of a 2-hydroxy-$\beta$-phenylpropiophenone of the formula II

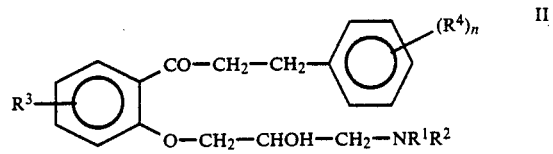

The reduction can be carried out catalytically or by reaction with a complex metal hydride.

For the catalytic reduction with hydrogen, catalysts such as $PtO_2$, Raney nickel, Pd/C or Pd/BaSO$_4$ can be used. Raney nickel and $PtO_2$ are preferably employed, the reaction preferably being carried out under neutral or basic conditions, and the reduction being terminated after one equivalent of hydrogen has been absorbed, in order to avoid further reduction. Hydrogenation can be carried out under atmospheric pressure or under superatmospheric pressure in a closed pressure-tight vessel, the former procedure being preferred. The reduction can be carried out at from room temperature to 100° C., preferably from 20° to 30° C. Suitable solvents for the reduction with hydrogen are primarily alcohols, such as methanol, ethanol or isopropanol. Examples of compounds which are suitable for the reduction with complex metal hydrides are $NaBH_4$, $LiAlH_4$, diborane, diborane/$BF_3$, lithium boranate, $Na[BH_3CN]$, $KBH_4$ and sodium bis-(2-methoxyethoxy)dihydridoaluminate, these being used in a protic or aprotic solvent. In a preferred embodiment, the reduction is carried out using NaBH₄ in methanol/H₂O or ethanol H₂O at from 20° to 50° C., or using LiAlH₄ in absolute ether, dioxane or tetrahydrofuran at from 20° C. to the reflux temperature of the solvent.

The starting compounds of the formula II which are required are known (cf. German Laid-Open Applications DOS No. 2,001,431, DOS No. 3,133,814 and DOS No. 3,226,863). They can be prepared from the corresponding 2-hydroxy-β-phenylpropiophenones by reaction with epichlorohydrin or epibromohydrin to give the glycidyl ether, followed by nucleophilic ring opening with the appropriate amine.

The novel compounds of the formula I possess a center of chirality at carbon atom 2 of the aliphatic side chain and at carbon atom 1 of the 1,3-diphenylpropanol, and as a rule are obtained in the form of a diastereomer mixture. The diastereomer pairs can be separated by fractional crystallization, and the racemates can be resolved into the optically active antipodes by a conventional method, for example by forming diastereomeric salts with optically active acids, such as dibenzoyltartaric acid, camphor-10-sulfonic acid, ditoluyltartaric acid or 3-bromocamphor-8-sulfonic acid.

The resulting compounds according to the invention can, if desired, be converted to addition salts with physiologically tolerated acids. Examples of conventional physiologically tolerated inorganic acids are hydrochloric acid, hydrobromic acid, phosphoric acid and sulfuric acid and examples of organic acids are oxalic acid, maleic acid, fumaric acid, lactic acid, tartaric acid, malic acid, citric acid, salicylic acid, adipic acid and benzoic acid. Other acids can be found in Fortschritte der Arzneimittelforschung, Volume 10, pages 224–225, Birkhäuser Verlag, Basel and Stuttgart, 1966.

As a rule, addition salts with acids are obtained in a conventional manner by mixing the free base, or a solution of this, with the appropriate acid, or a solution of this, in an organic solvent, for example a lower alcohol, such as methanol, ethanol or propanol, a lower ketone, such as acetone, methyl ethyl ketone or methyl isobutyl ketone, or an ether, such as diethyl ether, tetrahydrofuran or dioxane. In order to achieve better crystallization, mixtures of the above solvents can also be used. Moreover, pharmaceutically acceptable aqueous solutions of addition compounds of the aminopropanol derivatives of the formula I with acids can be prepared by dissolving the free base in an aqueous solution of the acid.

The novel compounds and their physiologically tolerated addition salts with acids possess antiarrhythmic, β-sympatholytic and Ca-antagonistic properties and can therefore be used, in particular, for the pharmacotherapeutic treatment of cardiac arrhythmias, the prevention of sudden cardiac death and the treatment of coronary diseases of the heart.

The following method was used in investigating the pharmacodynamic properties of the products according to the invention:

The substances were administered orally to Sprague-Dawley rats weighing 200–250 g. 45 minutes later, the animals were anesthetized with sodium thiobutabarbital (100 mg/kg, administered intraperitoneally). 60 minutes after administration of the substance, aconitine was infused intravenously, as the arrhythmogenic substance (dosage rate: 0.005 mg per kg per min.). In the case of untreated animals (N=52), arrhythmias appeared in the ECG after 2.74±0.07 min., the onset of these arrhythmias being delayed by antiarrhythmics in a dose-dependent manner.

The dose which prolonged the duration of infusion by 50%, i.e. the ED 50%, was determined from the linear relationship between log dose (mg/kg) of test substance and relative prolongation of the aconitine infusion duration (Δ%).

Furthermore, the dose at which toxic symptoms (changes in the initial ECG, cyanosis or cramp) occur was determined from the decimal-geometric dosage progression (factor $3\sqrt{10}$) used in the experiments. As a measure of the therapeutic index of the novel compounds, the quotient of the acute toxic dose and the antiarrhythmically effective dose (ED 50%) was determined.

When administered orally in doses of less than 46.4 mg/kg, the novel compounds exhibit antiarrhythmic β-sympatholytic and Ca-antagonistic activity. They are therefore clearly superior to the comparative substance propafenone [2-(2-hydroxy-3-propylaminopropoxy)-3-phenylpropiophenone hydrochloride].

The novel compounds can be administered in a conventional manner, either orally or intravenously. The dosage depends on the age, condition and weight of the patient and on the route of administration. As a rule, the daily dose of active compound is from about 5 to 75 mg/kg of body weight for oral administration, and from about 1 to 10 mg/kg of body weight for parenteral administration.

The novel compounds may be employed in the conventional solid or liquid pharmaceutical forms, e.g. tablets, film tables, capsules, powders, granules, coated tablets, suppositories or solutions. These are prepared in a conventional manner, and to do so the active compounds can be mixed with the conventional pharmaceutical auxiliaries, such as tablet binders, fillers, preservatives, tablet disintegraters, flow regulators, plasticizers, wetting agents, dispersants, emulsifiers, solvents, retarding agents and/or antioxidants (cf. H. Sucker et al., Pharmazeutische Technologie, Thieme-Verlag, Stuttgart, 1978). The resulting forms for administration generally contain from 1 to 99 percent by weight of the active compound.

The Examples which follow illustrate the invention.

A. Preparation of the starting compounds

EXAMPLE I 2-(2′,3′-Epoxypropoxy)-5-chloro-β-phenylpropiophenone 69 g (0.265 mole) of 2-hydroxy-5-chloro-β-phenylpropiophenone were stirred thoroughly with 125.4 g (0.915 mole) of epibromohydrin, 70 ml of dimethylformamide and 48.7 g (0.353 mole) of anhydrous K₂CO₃ for 5 hours at 60° C., after which the mixture was cooled, 250 ml of H₂O were added and the organic phase was freed from excess epibromohydrin by distillation under reduced pressure. The residue was recrystallized from cyclohexane/methyl tert.-butyl ether to give 67 g (79%) of product of melting point 46°–47° C.

EXAMPLE II 2-(2′-Hydroxy-3′-n-propylaminopropoxy)-5-chloro-β-phenylpropiophenone hydrochloride 5 g (0.016 mole) of 2-(2′,3′-epoxypropoxy)-5-chloro-β-phenylpropiophenone and 5 g (0.08 mole) of n-propylamine were dissolved in 100 ml of isopropanol, and the solution was kept on a waterbath for 8 hours. When the solution had cooled, the solvent and the excess amine were distilled off under reduced pressure, leaving 5.6 g of an oily residue, from which the hydrochloride was prepared using a solution of hydrochloric acid in ether. The hydrochloride was recrystallized from acetone/ether to give 4.7 g (71%) of product of melting point 163°–164° C.

B. Preparation of the compounds according to the invention

EXAMPLE 1

1-[2-(2'-Hydroxy-3'-n-propylaminopropoxy)-5-chlorophenyl]-3-phenylpropanol oxalate 6 g (0.014 mole) of 2-(2'-hydroxy-3'-n-propylaminopropoxy)-5-chloro-β-phenylpropiophenone were dissolved in 300 ml of a ≈3:1 ethanol/H₂O mixture, and 800 mg of NaBH₄ were added a little at a time. The solution was left to stand for 8 hours at room temperature, after which 500 ml of H₂O were added, the mixture was extracted several times with ether, the combined ether extracts were dried and the ether was distilled off under reduced pressure to give 5.5 g of an oily residue. The residue was taken up in ethanol, the calculated amount of oxalic acid was added and ethyl acetate was added until cloudiness occurred. The solution was left to stand for several days and then evaporated down, and the product was dried to give a white amorphous powder of melting point 55°–64° C.

EXAMPLE 2

1-[2-(2'-Hydroxy-3'-n-propylaminopropoxy)-phenyl]-3-phenylpropanol 10 g (0.03 mole) of 2-(2'-hydroxy-3'-n-propylaminopropoxy)-β-phenylpropiophenone were dissolved in 300 ml of ethanol, and were hydrogenated in the presence of 2 g of Pd/C under atmospheric pressure and at from 25° to 40° C., while stirring thoroughly. After 24 hours, the absorption of hydrogen was complete. The solution was then filtered off from the catalyst, and the solvent was distilled off under reduced pressure. The residue which remained was recrystallized from naphtha with the addition of a little acetone. 4.8 g (48%) of 1-[2-(2'-hydroxy-3-n-propylaminopropoxy)-phenyl]-3-phenylpropanol of melting point 86°–87° C. were isolated in this manner.

The following compounds were prepared by a method similar to that described in Example 1:

3. 1-[2-(2'-Hydroxy-3'-diisopropylaminopropoxy)-phenyl]-3-phenylpropanol tartrate, mp. 118° C.
4. 1-[2-(2'-Hydroxy-3'-piperidinopropoxy)-phenyl]-3-phenylpropanol oxalate, mp. 153° C.
5. 1-[2-(2'-Hydroxy-3'-(3-methyl-1-butyn-3-ylamino)-propoxy)-phenyl]-3-phenylpropanol oxalate, mp. 149° C.
6. 1-[2-(2'-Hydroxy-3'-(1-butyn-3-ylamino)-propoxy)-phenyl]-3-phenylpropanol oxalate, mp. 173° C.
7. 1-[2-(2'-Hydroxy-3'-(3-methoxyprop-2-ylamino)-propoxy)-phenyl]-3-phenylpropanol oxalate, mp. 153° C.
8. 1-[2-(2'-Hydroxy-3'-(N-methyl-N-(2-(3,4-dimethoxy-phenyl)-ethylamino)-propoxy)-phenyl]-3-phenyl-propanol oxalate, mp. 72° C.
9. 1-[2-(2'-Hydroxy-3'-(4-hydroxy-4-phenylpiperidino)-propoxy)-phenyl]-3-phenylpropanol, mp. 79° C.
10. 1-[2-(2'-Hydroxy-3'-(1,1-dimethylpropylamino)-propoxy)-phenyl]-3-phenylpropanol tartrate, amorphous
11. 1-[2-(2'-Hydroxy-3'-isopropylaminopropoxy)-phenyl]-3-phenylpropanol tartrate, amorphous
12. 1-[2-(2'-Hydroxy-3'-tert.-butylaminopropoxy)-phenyl]-3-phenylpropanol tartrate, amorphous
13. 1-[2-(2'-Hydroxy-3'-sec.-butylaminopropoxy)-phenyl]-3-phenylpropanol tartrate, amorphous
14. 1-[2-(2'-Hydroxy-3'-n-propylaminopropoxy)-phenyl]-3-(2-methoxyphenyl)-propanol oxalate, mp. 81°–95° C.
15. 1-[2-(2'-Hydroxy-3'-n-propylaminopropoxy)-phenyl]-3-(4-methylphenyl)-propanol oxalate, mp. 146° C.
16. 1-[2-(2'-Hydroxy-3'-n-propylaminopropoxy)-phenyl]-3-(4-chlorophenyl)-propanol oxalate, mp. 151°–154° C.
17. 1-[2-(2'-Hydroxy-3'-n-propylaminopropoxy)-phenyl]-3-(4-dimethylaminophenyl)-propanol bis-hydrochloride, mp. 50°–60° C.
18. 1-[2-(2'-Hydroxy-3'-n-propylaminopropoxy)-5-methylphenyl]-3-(3,4-dimethoxyphenyl)-propanol oxalate, mp. 136° C.
19. 1-[2-(2'-Hydroxy-3'-n-propylaminopropoxy)-phenyl]-3-(3,4-dimethoxyphenyl)-propanol oxalate, mp. 139°–141° C.
20. 1-[2-(2'-Hydroxy-3'-n-propylaminopropoxy)-5-methylphenyl]-3-(4-chlorophenyl)-propanol oxalate, mp. 173° C.

We claim:

1. An aminopropanol derivative of a 1-(2-hydroxyphenyl)-3-phenylpropanol of the formula I

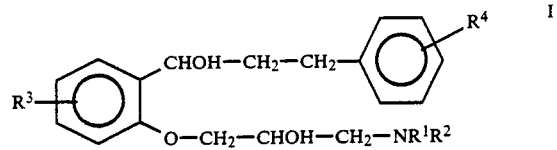

where $R^1$ and $R^2$ are identical or different and are each hydrogen, or alkyl, or alkynyl, each of not more than 6 carbon atoms, or a phenylalkyl radical where alkyl is of not more than 6 carbon atoms and the phenyl radical is substituted by alkoxy of not more than 3 carbon atoms, or $R^1$ and $R^2$, together with the nitrogen atom to which they are bonded, form a piperidino ring which is unsubstituted or substituted by 4-phenyl and 4-hydroxyl, $R^3$ is hydrogen, or alkyl of not more than 3 carbon atoms, $R^4$ is hydrogen, alkyl of not more than 3 carbon atoms, chlorine, or a radical $NR^5R^6$, where $R^5$ and $R^6$ are identical of different and are each alkyl of not more than 6 carbon atoms, and its physiologically tolerated addition salts with acids.

2. An aminopropanol derivative of the formula I as set forth in claim 1, which is 1-[2-(2'-hydroxy-3'-piperidinopropoxy)-phenyl]-3-phenylpropanol.

3. An aminopropanol derivative of the formula I as set forth in claim 1, which is 1-[2-(2'-hydroxy-3'-(4-hydroxy-4-phenylpiperidino)-propoxy)-phenyl]-3-phenylpropanol.

4. An aminopropanol derivative of the formula I as set forth in claim 1, which is 1-[2-(2'-hydroxy-3'-n-propylaminopropoxy)-phenyl]-3-(4-dimethylaminophenyl)-propanol bis-hydrochloride.

5. An aminopropanol derivative of the formula I as set forth in claim 1, which is 1-[2-(2'-hydroxy-3'-n-propylaminopropoxy)-phenyl]-3-phenylpropanol.

6. An aminopropanol derivative of the formula I as set forth in claim 1, which is 1-[2-(2'-hydroxy-3'-diisopropylaminopropoxy)-phenyl]-3-phenylpropanol.

7. An aminopropanol derivative of the formula I as set forth in claim 1, which is 1-[2-(2'-hydroxy-3'-(3-methyl-1-butyn-3-ylamino)-propoxy)phenyl]3-phenylpropanol.

8. An aminopropanol derivative of the formula I as set forth in claim 1, which is 1-[2-(2'-hydroxy-3'-(1-butyn-3-ylamino-propoxy-phenyl]-3-phenylpropanol.

9. An aminopropanol derivative of the formula I as set forth in claim 1, which is 1-[2-(2'-hydroxy-3'-(N-methyl-N-(2-(3,4-dimethoxyphenyl)ethylamino)-propoxy)-phenyl]-3-phenylpropanol.

10. An aminopropanol derivative of the formula I as set forth in claim 1, which is 1-[2-(2'-hydroxy-3'-tert.-butylaminopropoxy)-phenyl]-3-phenylpropanol.

11. An aminopropanol derivative of the formula I as set forth in claim 1, which is 1-[2-(2'-hydroxy-3'-n-propylaminopropoxy)-phenyl]-3-(4-methylphenyl)-propanol.

12. An aminopropanol derivative of the formula I as set forth in claim 1, which is 1-[2-(2'-hydroxy-3'-n-propylaminopropoxy)-5-methylphenyl]-3-(4-chlorophenyl)-propanol.

13. An aminopropanol derivative of the formula I as set forth in claim 1, wherein the derivative is in the form of a salt of oxalic acid.

14. An aminopropanol derivative of the formula I as set forth in claim 1, wherein the derivative is in the form of a salt of tartaric acid.

15. A therapeutic agent comprising a pharmaceutical excipient and an effective amount of a compound of the formula I according to claim 1 as the active compound.

16. The method of treating cardiac disorders in a patient suffering therefrom, which comprises administering an effective amount of a compound of the formula I according to claim 1.

* * * * *

UNITED STATES PATENT AND TRADEMARK OFFICE
CERTIFICATE OF CORRECTION

PATENT NO. : 4,612,320

DATED : September 16, 1986

INVENTOR(S) : Franke et al.

It is certified that error appears in the above-identified patent and that said Letters Patent is hereby corrected as shown below:

In the Claims: Correct the formula to read the following:

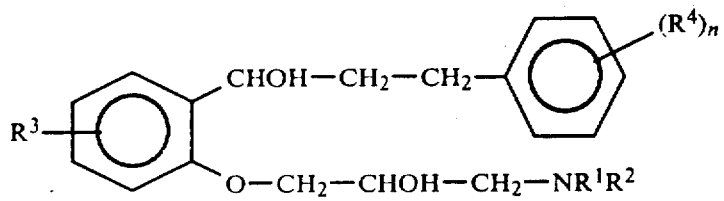

Column 6, line 52 should be <u>or not</u> [of]

Signed and Sealed this

Twenty-seventh Day of January, 1987

Attest:

DONALD J. QUIGG

Attesting Officer

Commissioner of Patents and Trademarks